United States Patent
Hilaire et al.

(10) Patent No.: US 8,814,925 B2
(45) Date of Patent: Aug. 26, 2014

(54) APPARATUS AND METHODS FOR STENT DELIVERY WITH EMBOLIC PROTECTION

(75) Inventors: Pierre Hilaire, Marly le Roi (FR); Machiel Van De Leest, Paris (FR)

(73) Assignee: Minvasys, Gennevilliers (FR)

( * ) Notice: Subject to any disclaimer, the term of this patent is extended or adjusted under 35 U.S.C. 154(b) by 1239 days.

(21) Appl. No.: 12/532,141

(22) PCT Filed: Mar. 20, 2008

(86) PCT No.: PCT/EP2008/053392
§ 371 (c)(1),
(2), (4) Date: Sep. 18, 2009

(87) PCT Pub. No.: WO2008/113857
PCT Pub. Date: Sep. 25, 2008

(65) Prior Publication Data
US 2010/0087908 A1    Apr. 8, 2010

Related U.S. Application Data

(60) Provisional application No. 60/919,034, filed on Mar. 20, 2007.

(51) Int. Cl.
*A61F 2/84* (2006.01)
*A61F 2/01* (2006.01)

(52) U.S. Cl.
CPC .......... *A61F 2/013* (2013.01); *A61F 2230/0093* (2013.01); *A61F 2230/0006* (2013.01); *A61F 2002/018* (2013.01); *A61F 2230/008* (2013.01)
USPC .......................................... 623/1.11; 606/200

(58) Field of Classification Search
CPC ................................. A61F 2/958; A61F 2/013
USPC ................ 606/191, 192, 194, 195, 198, 200; 623/1.11, 1.13, 1.15, 1.32, 1.39, 1.4, 623/1.44
See application file for complete search history.

(56) References Cited

U.S. PATENT DOCUMENTS

| | | | |
|---|---|---|---|
| 5,639,274 A * | 6/1997 | Fischell et al. | 606/194 |
| 6,152,946 A | 11/2000 | Broome et al. | |
| 6,171,328 B1 * | 1/2001 | Addis | 606/200 |
| 6,336,934 B1 | 1/2002 | Gilson et al. | |

(Continued)

FOREIGN PATENT DOCUMENTS

| EP | 1623680 | 2/2006 |
|---|---|---|
| WO | WO9717914 A1 | 5/1997 |

(Continued)

*Primary Examiner* — Brian Pellegrino
(74) *Attorney, Agent, or Firm* — GSS Law Group

(57) ABSTRACT

A catheter system including: a stent delivery catheter (2) having a proximal end and a distal end and an interior lumen extending between the proximal end and the distal end; a stent (1) having a proximal end and a distal end and a stent lumen extending between the proximal end and the distal end, the stent having an expanded state and an unexpanded state; and an embolic protection filter (3) having an expanded state and an unexpanded state; the catheter system having a deployed position and an undeployed position. When the catheter system is in the undeployed position, the stent (1) is in its unexpanded state and positioned within the interior lumen of the stent delivery catheter (2) and the embolic protection filter (3) is in its unexpanded state and positioned within the stent lumen of the stent.

27 Claims, 7 Drawing Sheets

(56) References Cited

U.S. PATENT DOCUMENTS

| | | |
|---|---|---|
| 7,172,621 B2 | 2/2007 | Thorn |
| 7,645,296 B2 | 1/2010 | Thorn et al. |
| 2002/0016624 A1* | 2/2002 | Patterson et al. ............ 623/1.12 |
| 2003/0055480 A1* | 3/2003 | Fischell et al. ............... 623/1.11 |
| 2006/0161241 A1* | 7/2006 | Barbut et al. ................ 623/1.15 |
| 2007/0055365 A1* | 3/2007 | Greenberg et al. .......... 623/1.44 |

FOREIGN PATENT DOCUMENTS

| | | | |
|---|---|---|---|
| WO | WO9922673 A1 | 5/1999 | |
| WO | WO9923976 A1 | 5/1999 | |
| WO | WO9944510 A1 | 9/1999 | |
| WO | WO9944542 A2 | 9/1999 | |
| WO | WO 2007067451 A2 * | 6/2007 | ................ A61F 2/02 |

\* cited by examiner

APPARATUS AND METHODS FOR STENT DELIVERY WITH EMBOLIC PROTECTION

This application is a U.S. national stage application filed under 35 U.S.C. 371 from PCT international application number PCT/EP2008/053392 filed on Mar. 20, 2008, which claims benefit of U.S. application No. 60/919,034 filed on Mar. 20, 2007.

FIELD OF THE INVENTION

The present invention relates generally to medical devices and in particular to catheter based devices for treating cardiovascular disease. The invention provides apparatus and methods for stent delivery with embolic protection. The invention is particularly useful for treating atherosclerotic disease of the carotid arteries, but can also be adapted for treating other areas of the vascular system.

BACKGROUND OF THE INVENTION

The following patent publications describe prior apparatus and methods for catheter based treatment of carotid artery stenosis. These and all patents and applications referred to therein are hereby incorporated by reference.

U.S. Pat. No. 7,172,621 Method of performing protected angioplasty and stenting at a carotid bifurcation U.S. Pat. No. 7,645,296 Catheter system for protected angioplasty and stenting at a carotid bifurcation

SUMMARY OF THE INVENTION

While there has been considerable progress in methods of treating cardiovascular disease with stent delivery system as illustrated by the above-mentioned documents, a need remains in the art to provide an improved catheter system which is easy to use for the physician and which enables efficient and safe stent deployment.

In its main aspect, the present invention is directed to a catheter system, comprising:

a stent delivery catheter having a proximal end and a distal end and an interior lumen extending between the proximal end and the distal end;

a stent having a proximal end and a distal end and a stent lumen extending between the proximal end and the distal end, the stent having an expanded state and an unexpanded state;

and an embolic protection filter having an expanded state and an unexpanded state;

the catheter system having a deployed position and an undeployed position characterized in that, when the catheter system is in the undeployed position, the stent is in its unexpanded state and positioned within the interior lumen of the stent delivery catheter and the embolic protection filter is in its unexpanded state and positioned within the stent lumen of the stent.

The originality of the catheter system according to the invention resides in the fact that the embolic protection filter is positioned within the stent lumen of the stent thus facilitating the use for the physician of the whole system comprising the stent and the filter.

According to one particular feature of the invention, when the catheter system is in the deployed position, the stent is in its expanded state and positioned exterior to the interior lumen of the stent delivery catheter and the embolic protection filter is in its expanded state and positioned within the stent lumen of the expanded stent.

In one preferred embodiment of the invention, the stent is a self-expanding stent.

In another embodiment of the invention, the catheter system further comprises a stent pusher catheter having a catheter shaft with a proximal end and a distal end and sized to fit within the interior lumen of the stent delivery catheter proximal to the stent, and the stent pusher catheter is configured to selectively deploy the catheter system by urging the stent from its unexpanded state within the interior lumen of the stent delivery catheter to its expanded state exterior to the interior lumen of the stent delivery catheter.

In another embodiment of the invention, the catheter system of the invention further comprises an inflatable angioplasty balloon mounted near the distal end of the catheter shaft of the stent pusher catheter.

According to one particular feature the stent pusher catheter has a shoulder at the distal end of the catheter shaft configured to bear against the proximal end of the stent.

In another embodiment of the invention, the catheter system further comprises a guidewire having a guidewire shaft, and the embolic protection filter is mounted on the guidewire shaft.

Advantageously, the embolic protection filter is slidably mounted on the guidewire shaft.

In another embodiment of the invention, the embolic protection filter comprises:

a filter member connected to a distal filter cylinder having an inner diameter $D_1$ larger than an outer diameter $d_2$ of the guidewire shaft;

a plurality of connecting wires having a first end connected to an outer periphery of the filter member and a second end connected to a proximal filter cylinder having an inner diameter $D_2$ larger than the outer diameter $d_2$ of the guidewire shaft;

and an actuation member attached to the guidewire shaft, the actuation member having an outer diameter $d_1$ that is larger than the outer diameter $d_2$ of the guidewire shaft and larger than the inner diameter $D_2$ of the proximal filter cylinder.

Advantageously, the inner diameter $D_1$ of the distal filter cylinder is larger than the outer diameter $d_1$ of the actuation member.

According to one particular feature, the actuation member comprises a radiopaque material.

In a further embodiment of the invention, the catheter system of the invention further comprises a catheter tip member attached to the embolic protection filter, wherein, when the catheter system is in the undeployed position, the catheter tip member is positioned to provide a smooth transition on the distal end of the stent delivery catheter for insertion of the catheter system into a patient.

According to a second aspect, the present invention is directed to a method of deploying a stent with embolic protection, comprising:

introducing into a patient a catheter system having:

a stent delivery catheter having a proximal end and a distal end and an interior lumen extending between the proximal end and the distal end;

a stent having a proximal end and a distal end and a stent lumen extending between the proximal end and the distal end, the stent having an expanded state and an unexpanded state;

and an embolic protection filter having an expanded state and an unexpanded state;

wherein the catheter system is in an undeployed position wherein the stent is in its unexpanded state and positioned within the interior lumen of the stent delivery catheter and the embolic protection filter is in its unexpanded state and positioned within the stent lumen of the stent;

and deploying the catheter system to a deployed position wherein the stent is in its expanded state and positioned exterior to the interior lumen of the stent delivery catheter and the embolic protection filter is in its expanded state and positioned within the stent lumen of the expanded stent.

According to one particular feature the method of the invention further comprises:

collapsing the embolic protection filter to its unexpanded state and withdrawing the embolic protection filter from the stent lumen of the expanded stent.

In one embodiment of the method, the catheter system is deployed using a stent pusher catheter positioned within the interior lumen of the stent delivery catheter to urge the stent from its unexpanded state within the interior lumen of the stent delivery catheter to its expanded state exterior to the interior lumen of the stent delivery catheter.

According to another particular feature the method of the invention further comprises:

advancing an angioplasty balloon mounted on the stent pusher catheter into the stent lumen of the expanded stent and inflating the angioplasty balloon within the stent lumen.

According to another particular feature the method of the invention further comprises:

deflating the angioplasty balloon and withdrawing the stent pusher catheter from the stent lumen of the expanded stent.

According to another particular feature the method of the invention further comprises:

collapsing the embolic protection filter to its unexpanded state and withdrawing the embolic protection filter from the stent lumen of the expanded stent.

In one embodiment, the catheter system used in carrying out the method of the invention further comprises a guidewire having a guidewire shaft, wherein the embolic protection filter is mounted on the guidewire shaft.

Advantageously, the embolic protection filter is slidably mounted on the guidewire shaft.

In a further embodiment, the embolic protection filter used in carrying out the method of the invention comprises:

a filter mesh connected to a distal filter cylinder having an inner diameter $D_1$ larger than an outer diameter $d_2$ of the guidewire shaft;

a plurality of connecting wires having a first end connected to an outer periphery of the filter mesh and a second end connected to a proximal filter cylinder having an inner diameter $D_2$ larger than the outer diameter $d_2$ of the guidewire shaft;

and an actuation member attached to the guidewire shaft, the actuation member having an outer diameter $d_1$ that is larger than the outer diameter $d_2$ of the guidewire shaft and larger than the inner diameter $D_2$ of the proximal filter cylinder; and the method further comprises:

withdrawing the guidewire shaft in a proximal direction with respect to the embolic protection filter such that the actuation member engages the proximal filter cylinder and collapses the embolic protection filter into a lumen of a filter retrieval catheter.

DETAILED DESCRIPTION OF THE INVENTION

The present invention provides apparatus and methods for stent delivery with embolic protection. The apparatus takes the form of a catheter system that includes a vascular stent, a stent delivery catheter and an integrated embolic protection filter. Optionally, the catheter system will also include a combination stent pusher and percutaneous transluminal angioplasty (PTA) balloon catheter. Alternatively, a simple stent pusher catheter can be provided and a separate PTA balloon catheter can be used for post dilatation if desired. The stent is preferably a self-expanding stent, but the catheter system can also be adapted for use of a balloon-expandable stent. The apparatus and methods of the invention are particularly useful for treating atherosclerotic disease of the carotid arteries, but can also be adapted for treating other areas of the vascular system.

Figure 1:
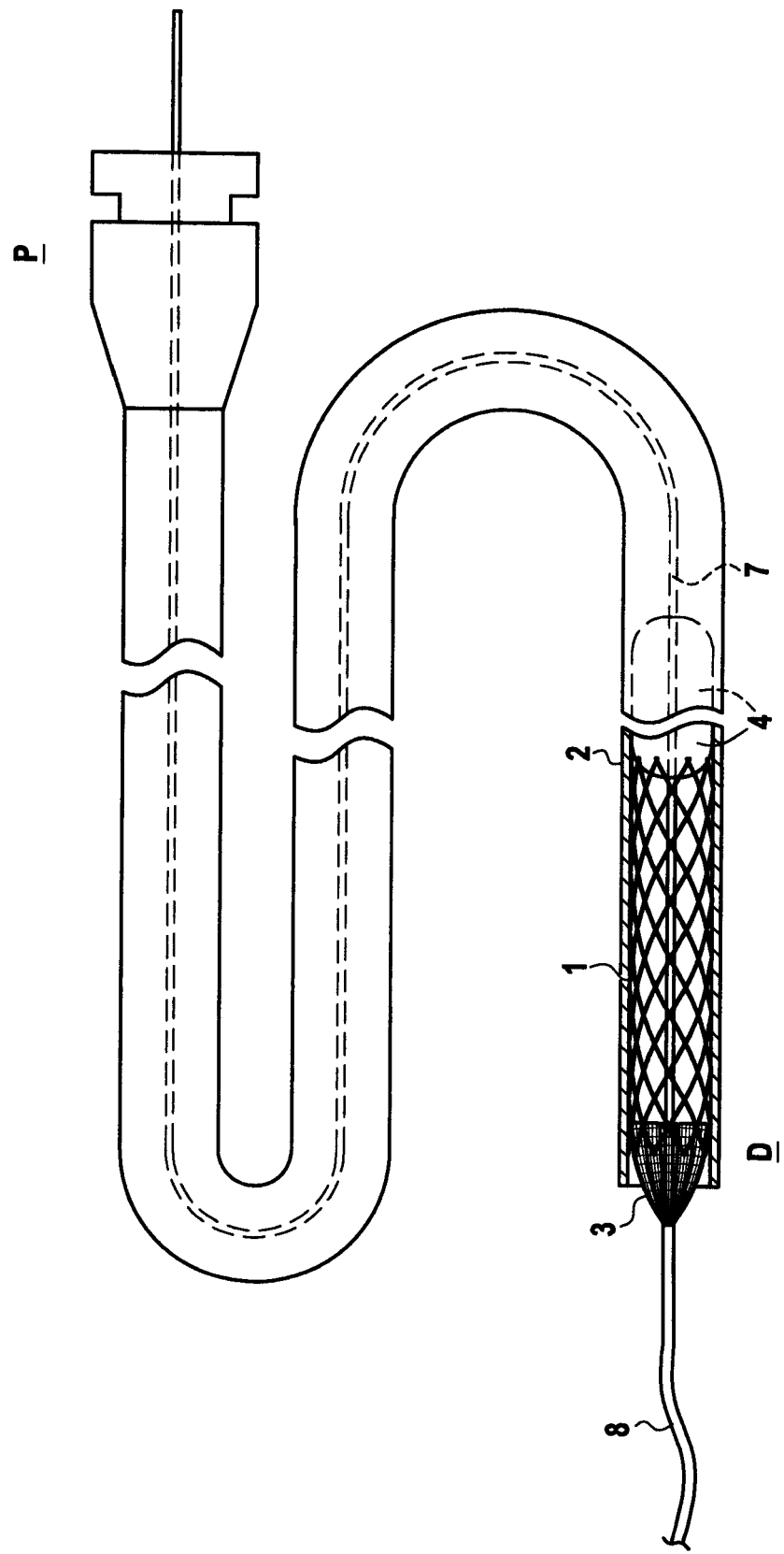
FIG. 1 illustrates a first embodiment of the stent delivery and embolic protection catheter system of the present invention shown in an undeployed position.

FIG. 1 illustrates a first embodiment of the stent delivery and embolic protection catheter system of the present invention which comprises a distal portion D and a proximal portion P where is located for instance a connector. The distal portion D of the catheter system is shown in an undeployed position. The catheter system includes a vascular stent 1, which is preferably a self-expanding stent, a stent delivery catheter 2, an integrated embolic protection filter 3 and, optionally, a combination stent pusher and PTA balloon catheter 4.

The stent 1 can be any know configuration of self-expanding vascular stent, for example a woven braided tubular stent of stainless steel, phynox, cobalt-chromium alloy or nickel-titanium alloy wire. The stent can also be formed by cutting a pattern of struts or supports out of a metallic tube or a metallic sheet, which is subsequently formed into tube or helix. Alternatively, the stent can be formed of a polymer or polymer composite. The stent can be coated or impregnated with an antiproliferative drug or other medication to prevent restenosis and/or thrombosis of the artery or other target vessel after treatment.

The embolic protection filter 3 is also preferably self-expanding so that the stent and filter can be deployed simultaneously with one simple motion and without requiring complicated manipulations by the user. Alternatively, the embolic protection filter can be manually deployable. The exemplary embolic protection filter 3 shown is configured as an umbrella with resilient radial struts 5 that support a filter mesh 6. The radial struts can be made of a resilient metal, such as stainless steel, cobalt-chromium alloy or nickel-titanium alloy wire, polymer or alloys and/or composites thereof. The struts 5 are attached in a radially extending configuration to a support shaft 7, such as the shaft of a steerable guidewire or the like. Preferably, the guidewire has a floppy distal part 8 to assist the catheter system to navigate through the vascular system and to cross the stenosis in the target artery. The filter mesh 6 is a flexible porous membrane of a polymer and/or metal and may be formed by weaving, or otherwise joining, fibers and/or wires into a membrane or by perforating a polymer or metal sheet. The filter mesh will preferably have a high percentage of open space so that it does not hinder blood flow through the vessel when deployed and will have a pore size chosen to capture potential emboli of a significant size that might cause damage in the cerebral vasculature. Pore size is preferably between 20 and 300 microns, more preferably between 60 and 100 microns.

Alternative configurations of the self-expanding embolic protection filter can include a conical or sac-shaped filter mesh supported by a resilient wire loop, which is attached to a guidewire shaft or the like.

The embolic protection filter is positioned within a distal portion of the self-expanding stent (see FIG. 2), then the stent and the embolic protection filter are radially compressed and inserted into the lumen of the stent delivery catheter, as shown in FIG. 1. The stent delivery catheter 2 is typically a thin-walled tubular plastic sheath. Suitable materials for the stent delivery catheter include, but are not limited to, polyimide, polyamide, polyethylene, polypropylene, fluoropolymers (e.g. PTFE, FEP, PFA, etc.) and copolymers, alloys and/or composites thereof.

Figure 2:
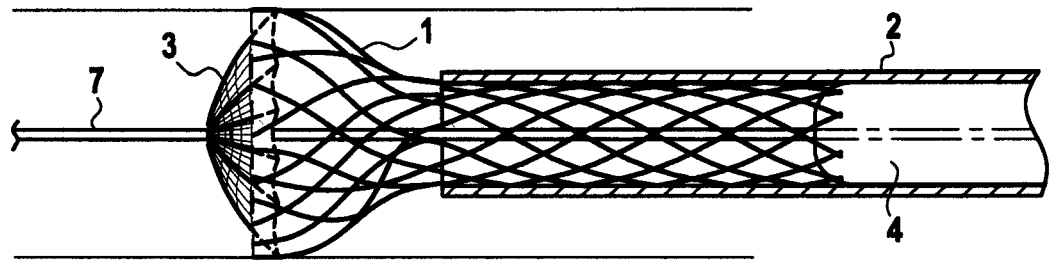
FIG. 2 shows the catheter system of FIG. 1 in a partially deployed position.

The PTA balloon catheter 4 is inserted into the lumen of the stent delivery catheter proximal to the compressed stent and filter. The PTA balloon catheter preferably is configured with a distal shoulder that allows it to serve as a stent pusher catheter as well, thereby simplifying the catheter system and the method of treatment. The stent and filter are deployed by pushing the stent out of the distal end of the stent delivery catheter using the distal shoulder of the combination stent pusher and PTA balloon catheter. FIG. 2 shows the catheter system of FIG. 1 in a partially deployed position. The self-expanding filter is passively deployed along with the stent, using one simple motion and without requiring complicated manipulations by the user. Because the embolic protection filter is deployed within the lumen of the stent, the potential complication of distal carotid artery spasm is avoided.

If desired, the PTA balloon catheter is advanced out of the stent delivery catheter and the balloon is inflated to perform a post-stenting angioplasty of any residual stenosis. The balloon is then deflated and the PTA balloon catheter is withdrawn into the stent delivery catheter.

Figure 3:
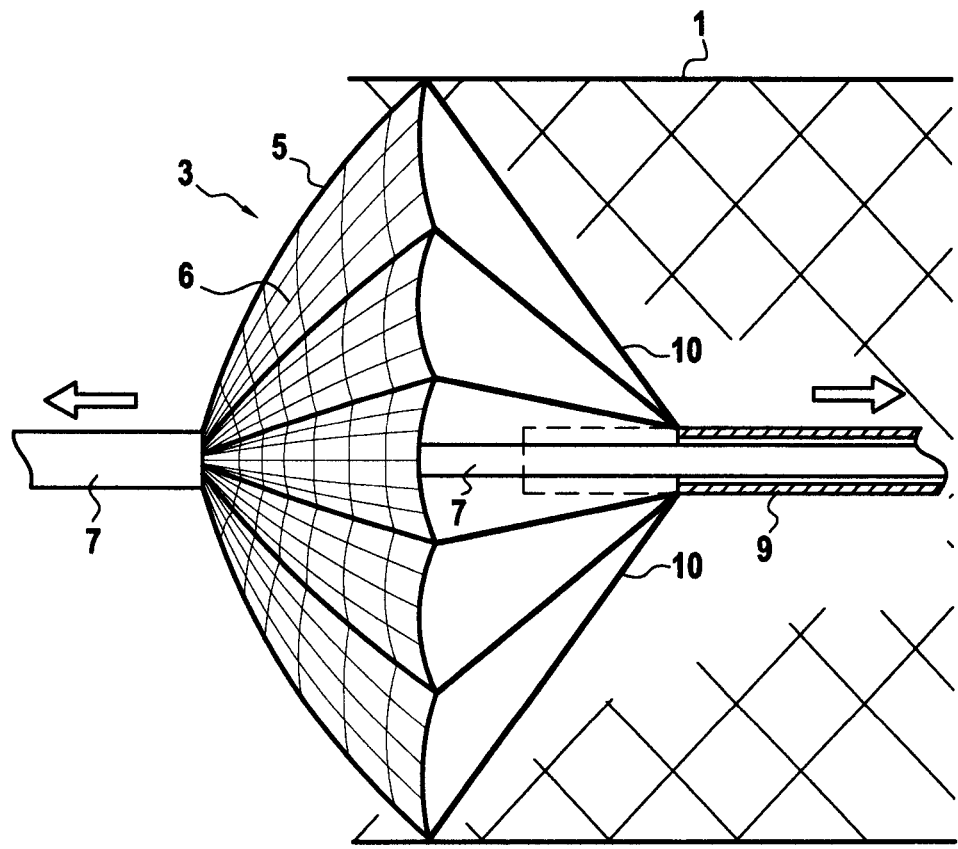
FIG. 3 shows the embolic protection filter being refolded for withdrawal from the stent after deployment.

Advantageously, the catheter system will include a mechanism for refolding or collapsing the embolic protection filter at the completion of the stenting procedure. In one exemplary embodiment, the catheter system includes a small diameter tube 9, for example an approximately 0.014 inch diameter metal or plastic tube, which is connected to the outer tips of the filter struts by connecting wires 10. By pushing on the shaft or stylet of the guidewire and pulling on the tube 9, the filter can be collapsed to a small enough diameter to withdraw it into the guiding catheter used to deliver the catheter system to the target artery. FIG. 3 shows the embolic protection filter being refolded for withdrawal from the stent after deployment.

Figure 4:
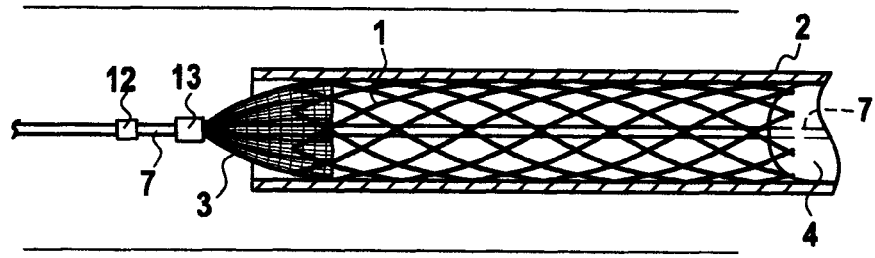
FIG. 4 illustrates a second embodiment of the stent delivery and embolic protection catheter system with a floating embolic protection filter shown in an undeployed position.
Figure 5:
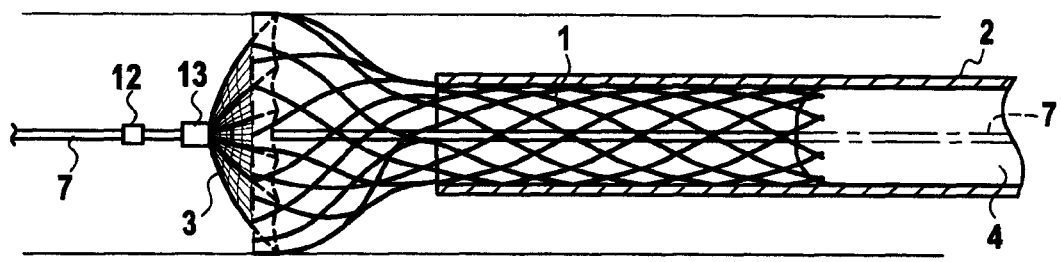
FIG. 5 shows the catheter system of FIG. 4 in a partially deployed position.

FIGS. 4-8 illustrate a second embodiment of the stent delivery and embolic protection catheter system of the present invention with the additional feature of a floating embolic protection filter. FIG. 4 shows the catheter system in an undeployed position. The self-expanding stent 1 and the embolic protection filter 3 are deployed similarly to the first embodiment described above. FIG. 5 shows the catheter system of FIG. 4 in a partially deployed position. The floating embolic protection filter allows the guidewire 7 to be manipulated independently of the filter 3 during insertion of the catheter system. It also helps to avoid accidental dislodgement of the filter after deployment by allowing a range of free play between the filter and guidewire on which it is mounted. If desired, the guidewire 7 can be inserted separately from the rest of catheter system and followed up with the filter 3 and the stent delivery catheter 2. Thus, the same guidewire could be used to guide insertion of a pre-dilatation catheter, the stent delivery catheter and, optionally, a post-dilatation catheter.

Optionally, the fixed position or floating embolic protection filter can be inserted into a distal portion of the stent prior to compressing it into the undeployed position within the lumen of the stent delivery catheter so that the filter 3 will deploy automatically upon deployment of the stent 1, as shown in FIG. 1-2 or 4-5. Alternatively, the embolic protection filter can be positioned distal to the stent within the lumen of the stent delivery catheter so that the filter can be automatically deployed upon deployment of the stent or deployed manually within the target vessel before deploying the stent.

The fixed-position or floating embolic protection filter can also be used separately from the catheter system or adapted to provide embolic protection with other catheters and catheter systems. For example, the floating embolic protection filter could be adapted for use with a balloon expandable stent delivery system.

Figure 6:
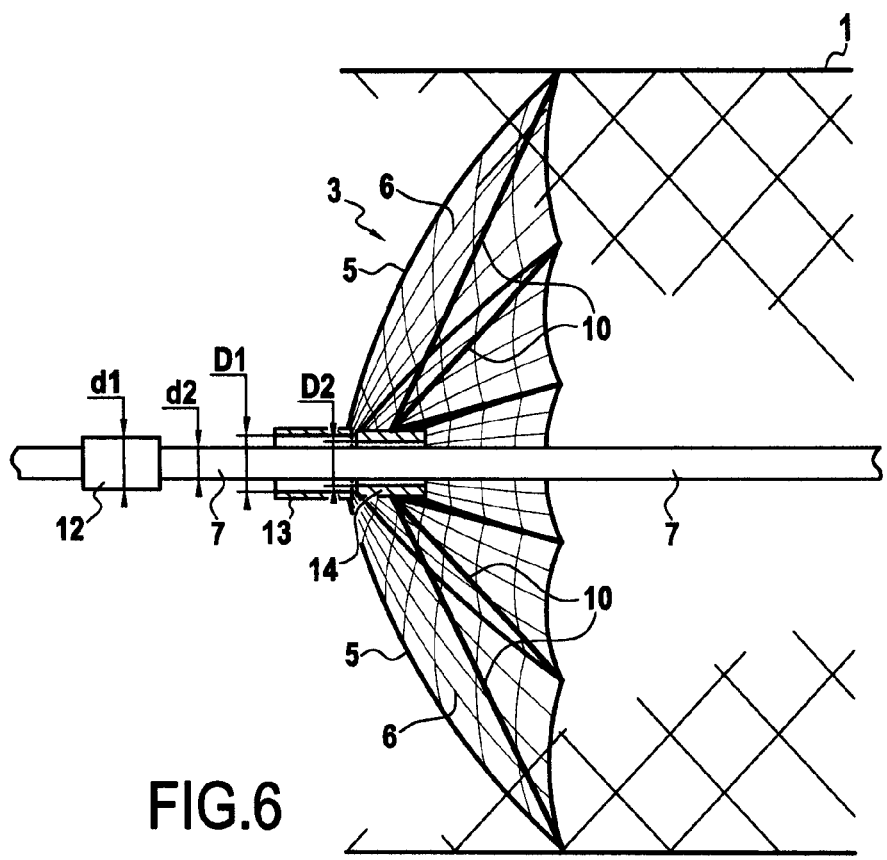
FIGS. 6-8 show the embolic protection filter being refolded for withdrawal from the stent after deployment.

FIG. 6 shows the embolic protection filter in a deployed position within the lumen of the deployed vascular stent. An actuation member 12 with an outer diameter $d_1$, which is slightly larger than the outer diameter $d_2$ of the shaft or stylet of the guidewire 7, is attached to the shaft or stylet of the guidewire. Advantageously, the actuation member 12 can be configured as a radiopaque marker band attached to the shaft or stylet of the guidewire, as shown. Alternatively, an increased diameter portion of the guidewire shaft or the floppy distal portion of the guidewire may serve as an actuation member.

The radial filter struts 5 are attached to a distal filter cylinder 13, which has an inner diameter $D_1$ slightly larger than the outer diameter $d_1$ of the actuation member. Similarly, the connecting wires 10 of the filter 3 are connected to a proximal filter cylinder 14, which has an inner diameter $D_2$ slightly smaller than the outer diameter $d_1$ of the actuation member. Because the inner diameters of the distal filter cylinder $D_1$ and the proximal filter cylinder $D_2$ are larger than the outer diameter $d_2$ of the shaft or stylet of the guidewire, the filter 3 is free to float, i.e. move longitudinally, with respect to the guidewire 7 and vice versa. The movement of the filter in the distal direction is limited by the fact that the outer diameter $d_1$ of the actuation member 12 is larger than the inner diameter $D_2$ of the proximal filter cylinder 14.

Optionally, the embolic protection filter may be initially configured with the proximal filter cylinder 14 adjacent to the distal filter cylinder 13 (see FIG. 6), which allows a slightly smaller undeployed diameter of the catheter system.

Figure 7:
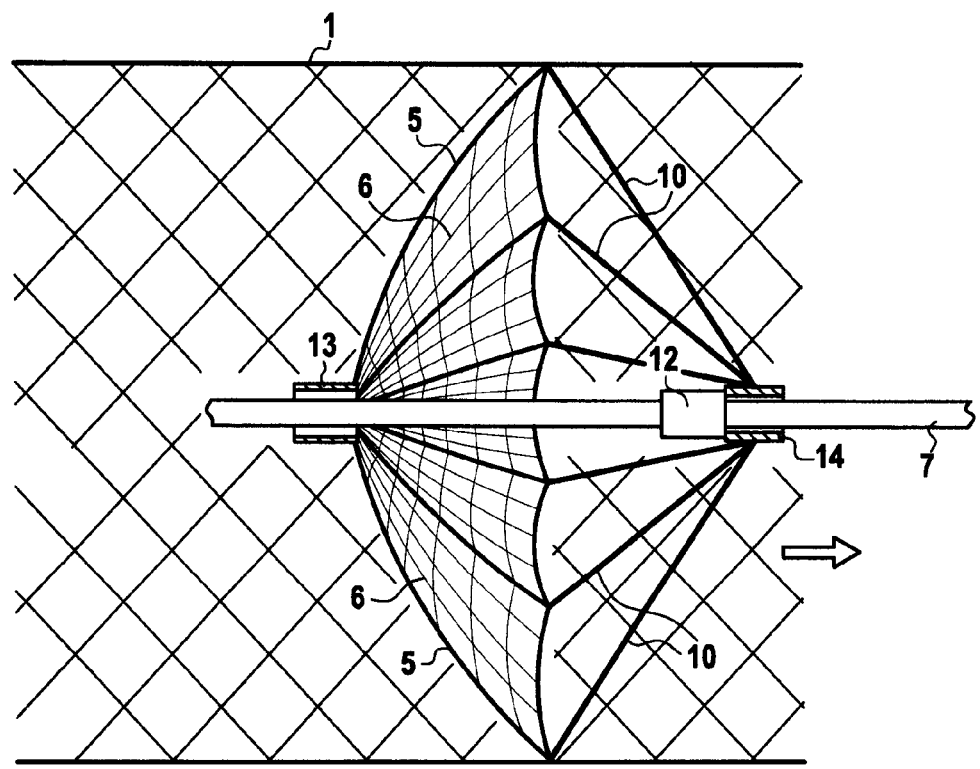
Figure 8:
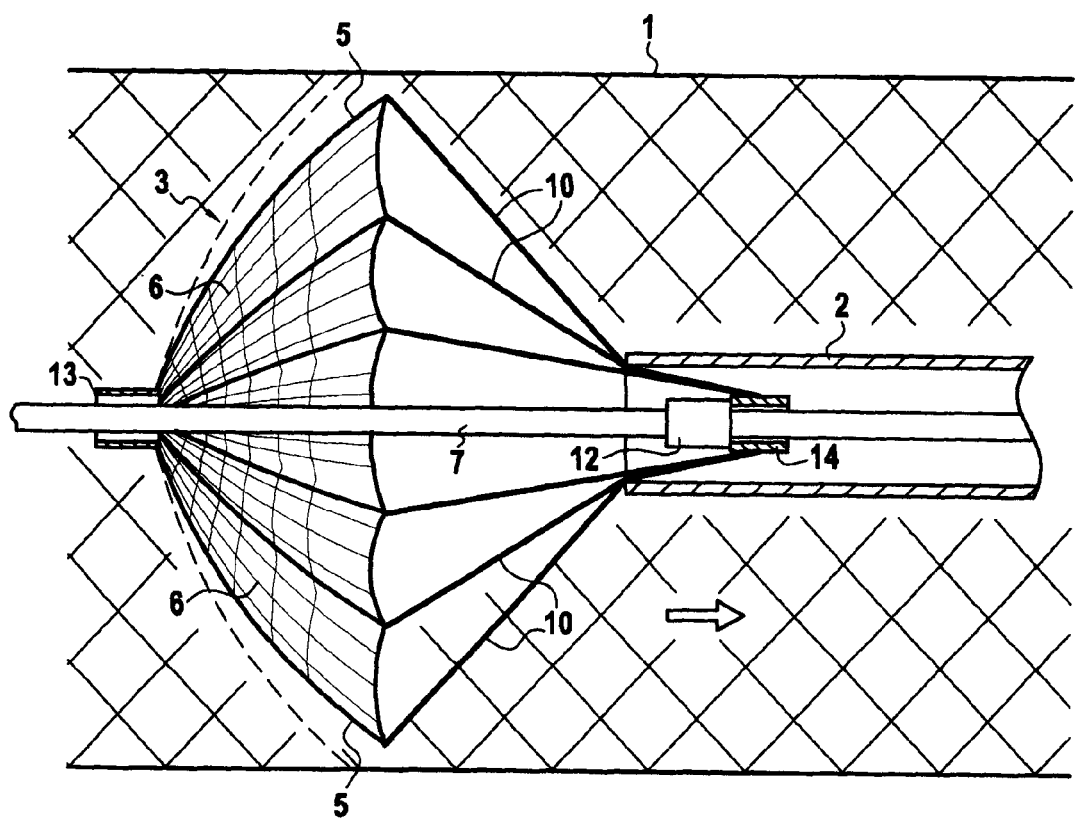

FIGS. 6-8 show the embolic protection filter being refolded for withdrawal from the stent after deployment. Starting from the deployed position in FIG. 6, the guidewire 7 is withdrawn proximally until the actuation member 12 engages the proximal filter cylinder 13. The proximal filter cylinder moves proximally with respect to the filter, which is held in place by friction with the deployed stent. The connecting wires 10 move into a position effective for refolding the filter 3, as shown in FIG. 7. Next, the guiding catheter or a separate filter retrieval catheter is advanced distally while maintaining tension on the guidewire 7, as shown in FIG. 8. The filter folds as it is withdrawn into the lumen of the guiding catheter 2 or a separate filter retrieval catheter. If a separate filter retrieval catheter is used it may be configured as an over-the-wire or rapid exchange catheter.

The embolic protection filter 3 can be configured to facilitate refolding of the filter. A smooth transition between the connecting wires and the radial struts of the filter will help the filter slide smoothly into the lumen of the guiding catheter when tension is applied to the connecting wires through the proximal filter cylinder. Additionally, if the connecting wires 10 are optionally configured to have a higher bending stiffness than the filter struts, the connecting wires will act as levers to push the filter toward a closed position as the connecting wires are withdrawn into the lumen of the guiding catheter.

Figure 9:
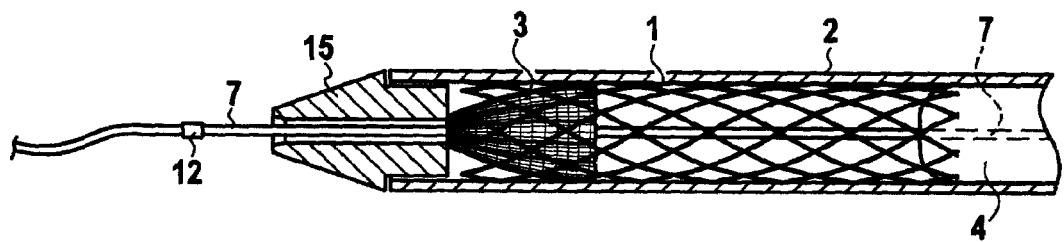
FIG. 9 illustrates a third embodiment of the stent delivery and embolic protection catheter system with a soft tip on the embolic protection filter shown in an undeployed position.

FIG. 9 illustrates a third embodiment of the stent delivery and embolic protection catheter system with a soft tip 15 attached to the embolic protection filter. This optional feature may be combined with the features of any of the other embodiments described herein. The soft tip provides a smooth transition on the distal end of the stent delivery catheter during insertion of the catheter system. In one exemplary embodiment shown in FIG. 9, the soft tip 15 is positioned distally of the compressed stent 1 in the undeployed position. Suitable materials for the soft tip include, but are not limited to, polyamide, polyamide copolymers (e.g. PEBAX), polyurethane, silicone, Kraton, polyethylene, ethylene vinyl acetate, polypropylene, fluoropolymers (e.g. PTFE, FEP, PFA, etc.) and copolymers, alloys and/or composites thereof.

Figure 10:
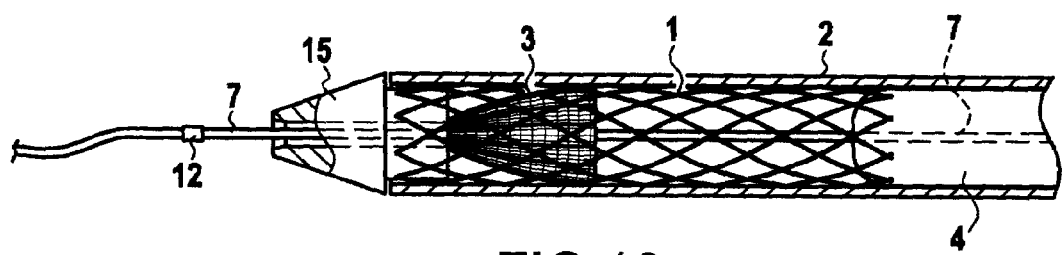
FIG. 10 illustrates an alternative configuration of the stent delivery and embolic protection catheter system with a soft tip on the embolic protection filter shown in an undeployed position.

FIG. 10 illustrates an alternative configuration of the stent delivery and embolic protection catheter system with a soft tip 15. In this embodiment, the soft tip is positioned inside a distal portion of the compressed stent when in the undeployed position.

Figure 11:
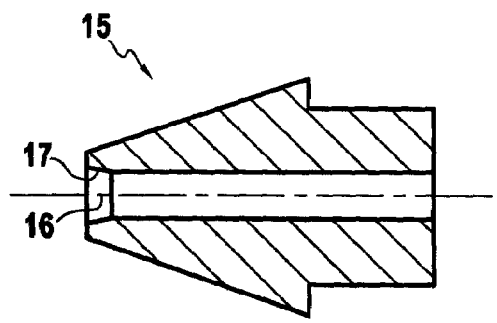
FIG. 11 is an enlarged detail drawing of the soft tip of the embolic protection filter.

FIG. 11 is an enlarged detail drawing of the soft tip of the embolic protection filter. The distal end of the soft tip has a conical or bullet-shaped exterior that is sized to provide a smooth transition with the distal end of the stent delivery catheter. A lumen 16 extends through the soft tip to accommodate the shaft of the guidewire 7 on which the embolic protection filter is mounted. If the catheter system uses a fixed position filter, then the lumen can have a tight fit on the shaft of the guidewire. If the catheter system uses a floating filter, then the lumen should be large enough in diameter to allow passage of the actuation member on the shaft of the guidewire. Preferably, an internal cone 17 is provided on the distal end of the lumen to facilitate entry and passage of the actuation member.

Figure 12:
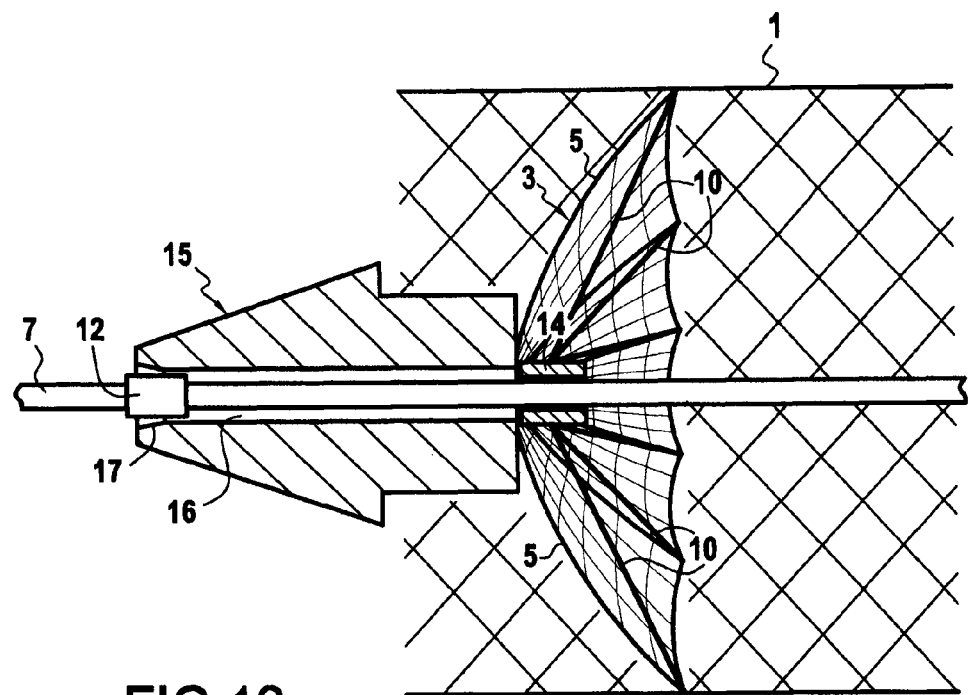
FIG. 12 shows the catheter system of FIG. 9 in a deployed position.

FIG. 12 shows the catheter system of FIG. 9 in a deployed position with the expanded embolic protection filter with a soft tip positioned within the lumen of the expanded stent.

Figure 13:
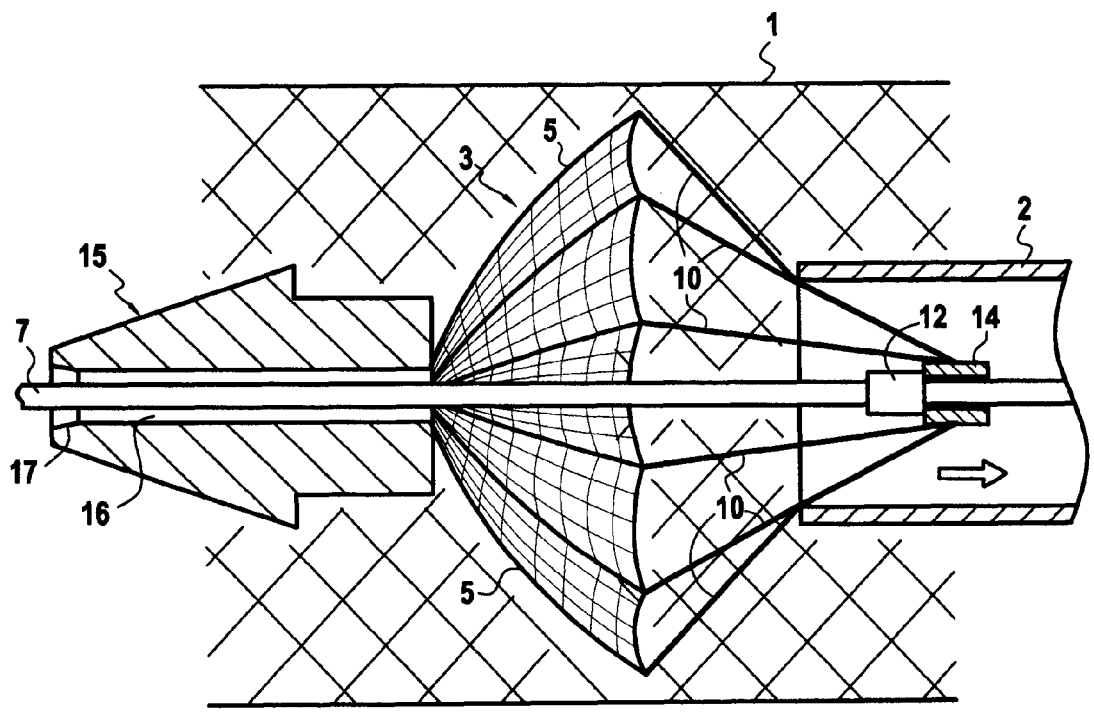
FIG. 13 shows the embolic protection filter being refolded for withdrawal from the stent after deployment.

FIG. 13 shows a floating embolic protection filter with a soft tip being refolded and withdrawn into the lumen of the guiding catheter for withdrawal from the stent after deployment.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

The invention claimed is:

1. A catheter system, comprising:
a stent delivery catheter having a proximal end and a distal end and an interior lumen extending between the proximal end and the distal end;
a stent having a proximal end and a distal end and a stent lumen extending between the proximal end and the distal end, the stent having an expanded state and an unexpanded state;
and an embolic protection filter having an expanded state and an unexpanded state;
the catheter system having a deployed position and an undeployed position,
a guidewire having a guidewire shaft, wherein the embolic protection filter is slidably mounted on the guidewire shaft;
wherein the embolic protection filter comprises:
a filter member connected to a distal filter cylinder having an inner diameter $D_1$ larger than an outer diameter $d_2$ of the guidewire shaft;
a plurality of connecting wires having a first end connected to an outer periphery of the filter member and a second end connected to a proximal filter cylinder having an inner diameter $D_2$ larger than the outer diameter $d_2$ of the guidewire shaft;
and an actuation member attached to the guidewire shaft, the actuation member having an outer diameter $d_1$ that is larger than the outer diameter $d_2$ of the guidewire shaft and larger than the inner diameter $D_2$ of the proximal filter cylinder;
wherein, when the catheter system is in the undeployed position, the stent is in its unexpanded state and positioned within the interior lumen of the stent delivery catheter and the embolic protection filter is in its unexpanded state and positioned within the stent lumen of the stent.

2. The catheter system of claim 1, wherein, when the catheter system is in the deployed position, the stent is in its expanded state and positioned exterior to the interior lumen of the stent delivery catheter and the embolic protection filter is in its expanded state and positioned within the stent lumen of the expanded stent.

3. The catheter system of claim 2, further comprising a stent pusher catheter having a catheter shaft with a proximal end and a distal end and sized to fit within the interior lumen of the stent delivery catheter proximal to the stent, wherein the stent pusher catheter is configured to selectively deploy the catheter system by urging the stent from its unexpanded state within the interior lumen of the stent delivery catheter to its expanded state exterior to the interior lumen of the stent delivery catheter.

4. The catheter system of claim 3, further comprising an inflatable angioplasty balloon mounted near the distal end of the catheter shaft of the stent pusher catheter.

5. The catheter system of claim 4, wherein the stent pusher catheter has a shoulder at the distal end of the catheter shaft configured to bear against the proximal end of the stent.

6. The catheter system of claim 1, wherein the stent is a self-expanding stent.

7. The catheter system of claim 1, wherein the actuation member comprises a radiopaque material.

8. The catheter system of claim 1, further comprising a catheter tip member attached to the embolic protection filter, wherein, when the catheter system is in the undeployed position, the catheter tip member is positioned to provide a smooth transition on the distal end of the stent delivery catheter for insertion of the catheter system into a patient.

9. The catheter system of claim 1, further comprising a stent pusher catheter having a catheter shaft with a proximal end and a distal end and sized to fit within the interior lumen of the stent delivery catheter proximal to the stent, wherein the stent pusher catheter is configured to selectively deploy the catheter system by urging the stent from its unexpanded state within the interior lumen of the stent delivery catheter to its expanded state exterior to the interior lumen of the stent delivery catheter.

10. The catheter system of claim 1, further comprising:
a stent pusher catheter having a catheter shaft with a proximal end and a distal end, the catheter shaft sized to fit within the interior lumen of the stent delivery catheter proximal to the stent, a shoulder at the distal end of the catheter shaft configured to bear against the proximal end of the stent,
and an inflatable angioplasty balloon mounted near the distal end of the catheter shaft of the stent pusher catheter,
wherein the stent pusher catheter is configured to selectively deploy the catheter system by urging the stent from its unexpanded state within the interior lumen of the stent delivery catheter to its expanded state exterior to the interior lumen of the stent delivery catheter.

11. A catheter system, comprising:
a stent delivery catheter having a proximal end and a distal end and an interior lumen extending between the proximal end and the distal end;
a stent having a proximal end and a distal end and a stent lumen extending between the proximal end and the distal end, the stent having an expanded state and an unexpanded state;
and an embolic protection filter having an expanded state and an unexpanded state;
the catheter system having a deployed position and an undeployed position,
a guidewire having a guidewire shaft, wherein the embolic protection filter is slidably mounted on the guidewire shaft;
wherein the embolic protection filter comprises:
a filter member connected to a distal filter cylinder having an inner diameter $D_1$ larger than an outer diameter $d_2$ of the guidewire shaft;
a plurality of connecting wires having a first end connected to an outer periphery of the filter member and a second end connected to a proximal filter cylinder having an inner diameter $D_2$ larger than the outer diameter $d_2$ of the guidewire shaft;
and an actuation member attached to the guidewire shaft, the actuation member having an outer diameter $d_1$ that is larger than the outer diameter $d_2$ of the guidewire shaft and larger than the inner diameter $D_2$ of the proximal filter cylinder;
wherein the inner diameter $D_1$ of the distal filter cylinder is larger than the outer diameter $d_1$ of the actuation member.

12. The catheter system of claim 11, wherein the actuation member comprises a radiopaque material.

13. The catheter system of claim 11, further comprising a catheter tip member attached to the embolic protection filter, wherein, when the catheter system is in the undeployed position, the catheter tip member is positioned to provide a smooth transition on the distal end of the stent delivery catheter for insertion of the catheter system into a patient.

14. A catheter system, comprising:

a stent delivery catheter having a proximal end and a distal end and an interior lumen extending between the proximal end and the distal end;
a self-expandable stent having a proximal end and a distal end and a stent lumen extending between the proximal end and the distal end, the stent having an expanded state and an unexpanded state;
and a self-expandable embolic protection filter having an expanded state and an unexpanded state;
a stent pusher catheter having a catheter shaft with a proximal end and a distal end and sized to fit within the interior lumen of the stent delivery catheter proximal to the stent, the stent pusher catheter having a shoulder at the distal end of the catheter shaft configured to bear against the proximal end of the stent, wherein the stent pusher catheter is configured to selectively deploy the catheter system by urging the stent from its unexpanded state within the interior lumen of the stent delivery catheter to its expanded state exterior to the interior lumen of the stent delivery catheter;
an inflatable angioplasty balloon mounted near the distal end of the catheter shaft of the stent pusher catheter;
the catheter system having a deployed position and an undeployed position, wherein, when the catheter system is in the undeployed position, the stent is in its unexpanded state and positioned within the interior lumen of the stent delivery catheter and the embolic protection filter is in its unexpanded state and positioned within the stent lumen of the stent.

15. The catheter system of claim 14, wherein, when the catheter system is in the deployed position, the stent is in its expanded state and positioned exterior to the interior lumen of the stent delivery catheter and the embolic protection filter is in its expanded state and positioned within the stent lumen of the expanded stent.

16. The catheter system of claim 14, further comprising a guidewire having a guidewire shaft, wherein the embolic protection filter is mounted on the guidewire shaft.

17. The catheter system of claim 16, wherein the embolic protection filter is slidably mounted on the guidewire shaft.

18. A method of deploying a stent with embolic protection utilizing the catheter system of claim 14, the method comprising:
introducing the catheter system into a patient;
and deploying the catheter system to the deployed position wherein the stent is in its expanded state and positioned exterior to the interior lumen of the stent delivery catheter and the embolic protection filter is in its expanded state and positioned within the stent lumen of the expanded stent.

19. The method of claim 18, further comprising:
collapsing the embolic protection filter to its unexpanded state and withdrawing the embolic protection filter from the stent lumen of the expanded stent.

20. The method of claim 18, wherein the catheter system is deployed using the stent pusher catheter positioned within the interior lumen of the stent delivery catheter to urge the stent from its unexpanded state within the interior lumen of the stent delivery catheter to its expanded state exterior to the interior lumen of the stent delivery catheter.

21. The method of claim 20, further comprising:
advancing the angioplasty balloon mounted on the stent pusher catheter into the stent lumen of the expanded stent and inflating the angioplasty balloon within the stent lumen.

22. The method of claim 21, further comprising:

deflating the angioplasty balloon and withdrawing the stent pusher catheter from the stent lumen of the expanded stent.

23. The method of claim 18, wherein the catheter system further comprises a guidewire having a guidewire shaft, wherein the embolic protection filter is mounted on the guidewire shaft.

24. The method of claim 23, wherein the embolic protection filter is slidably mounted on the guidewire shaft.

25. The method of claim 24, wherein the embolic protection filter comprises:
- a filter mesh connected to a distal filter cylinder having an inner diameter $D_1$ larger than an outer diameter $d_2$ of the guidewire shaft;
- a plurality of connecting wires having a first end connected to an outer periphery of the filter mesh and a second end connected to a proximal filter cylinder having an inner diameter $D_2$ larger than the outer diameter $d_2$ of the guidewire shaft;
- and an actuation member attached to the guidewire shaft, the actuation member having an outer diameter $d_1$ that is larger than the outer diameter $d_2$ of the guidewire shaft and larger than the inner diameter $D_2$ of the proximal filter cylinder;

and wherein the method further comprises:
withdrawing the guidewire shaft in a proximal direction with respect to the embolic protection filter such that the actuation member engages the proximal filter cylinder and collapses the embolic protection filter into a lumen of a filter retrieval catheter.

26. The method of claim 25, wherein the catheter system further comprises a catheter tip member attached to the embolic protection filter, wherein, when the catheter system is in the undeployed position, the catheter tip member is positioned to provide a smooth transition on the distal end of the stent delivery catheter for insertion of the catheter system into a patient.

27. The method of claim 18, wherein the catheter system further comprises a catheter tip member attached to the embolic protection filter, wherein, when the catheter system is in the undeployed position, the catheter tip member is positioned to provide a smooth transition on the distal end of the stent delivery catheter for insertion of the catheter system into a patient.

* * * * *